United States Patent
Egan

(10) Patent No.: US 11,116,179 B2
(45) Date of Patent: Sep. 14, 2021

(54) OVINE PROTECTOR

(71) Applicant: Margaret Egan, Tynong (AU)

(72) Inventor: Margaret Egan, Tynong (AU)

( * ) Notice: Subject to any disclaimer, the term of this patent is extended or adjusted under 35 U.S.C. 154(b) by 57 days.

(21) Appl. No.: 15/552,208

(22) PCT Filed: Feb. 19, 2016

(86) PCT No.: PCT/AU2016/000056
§ 371 (c)(1),
(2) Date: Aug. 18, 2017

(87) PCT Pub. No.: WO2016/131089
PCT Pub. Date: Aug. 25, 2016

(65) Prior Publication Data
US 2018/0027767 A1 Feb. 1, 2018

(30) Foreign Application Priority Data
Feb. 20, 2015 (AU) .................................. 2015900608

(51) Int. Cl.
*A01K 13/00* (2006.01)
*A61D 9/00* (2006.01)
(Continued)

(52) U.S. Cl.
CPC .............. *A01K 13/006* (2013.01); *A61D 9/00* (2013.01); *A61F 7/02* (2013.01);
(Continued)

(58) Field of Classification Search
CPC .... A01K 13/006; A01K 13/008; A01K 13/00; B68C 2005/005; A61D 9/00; A61F 7/02;
(Continued)

(56) References Cited

U.S. PATENT DOCUMENTS

| | | | |
|---|---|---|---|
| 1,218,004 A | 3/1917 | Sayles | |
| 1,612,945 A * | 1/1927 | Rieck | A01K 13/006 54/79.2 |

(Continued)

FOREIGN PATENT DOCUMENTS

| | | | |
|---|---|---|---|
| GB | 982010 A * | 2/1965 | .......... A01K 13/006 |
| GB | 2374535 | 3/2003 | |

(Continued)

OTHER PUBLICATIONS

Written Opinion and International Search Report for International Patent Application No. PCT/AU2016/000056, dated Mar. 16, 2016.

*Primary Examiner* — Christopher D Hutchens
(74) *Attorney, Agent, or Firm* — Kim IP Law Group LLC

(57) ABSTRACT

An ovine protector for a newborn ovine including a shaped body wrap having a body cover portion, the shaped body providing a protection from the weather; a connection system connecting at extremities the shaped body wrap to the newborn ovine, the connection system having a triangular arrangement between a front collar connection and two separate rear leg connections; and wherein the protector provides a covering over the newborn ovine with an open rear and open underneath by the connection system.

20 Claims, 10 Drawing Sheets

(51) Int. Cl.
*A61F 7/02* (2006.01)
*A61F 7/00* (2006.01)

(52) U.S. Cl.
CPC . *A61F 2007/0001* (2013.01); *A61F 2007/023* (2013.01); *A61F 2007/0244* (2013.01)

(58) Field of Classification Search
CPC ........ A61F 2007/0001; A61F 2007/023; A61F 2007/0244
USPC ................................ 119/850, 859; D30/145
See application file for complete search history.

(56) References Cited

U.S. PATENT DOCUMENTS

| | | | | | |
|---|---|---|---|---|---|
| 2,131,495 | A | * | 9/1938 | Allen | A01K 13/006 54/79.2 |
| 2,850,860 | A | * | 9/1958 | Torell | A01K 13/006 54/79.2 |
| 4,671,049 | A | * | 6/1987 | Benckhuijsen | A01K 13/008 54/79.4 |
| 5,165,222 | A | | 11/1992 | Cohen et al. | |
| 5,537,954 | A | * | 7/1996 | Beeghly | A01K 13/006 119/850 |
| D511,868 | S | * | 11/2005 | Cherrett | D30/145 |
| D613,001 | S | * | 3/2010 | OBrien | D30/145 |
| 9,386,759 | B2 | * | 7/2016 | Russakoff | A01K 13/008 |
| 2005/0126134 | A1 | * | 6/2005 | Hathcock | A01K 13/008 54/79.2 |
| 2005/0211192 | A1 | | 9/2005 | Nilforushan | |
| 2006/0169221 | A1 | * | 8/2006 | Teague | A01K 13/006 119/850 |
| 2007/0289557 | A1 | * | 12/2007 | Gerdes | A01K 13/006 119/850 |
| 2007/0289558 | A1 | * | 12/2007 | Bonfoey | A01K 13/006 119/850 |
| 2008/0067163 | A1 | * | 3/2008 | Axinte | A01K 13/006 219/211 |
| 2008/0110414 | A1 | * | 5/2008 | Buehner | A01K 13/006 119/712 |
| 2010/0161015 | A1 | * | 6/2010 | Wilson | A61F 7/02 607/112 |
| 2011/0162589 | A1 | | 7/2011 | Singer et al. | |
| 2013/0160720 | A1 | * | 6/2013 | Corcoran | A01K 13/006 119/850 |
| 2015/0208611 | A1 | * | 7/2015 | Russakoff | A01K 13/008 54/79.2 |
| 2016/0174523 | A1 | * | 6/2016 | Neveu | A01K 13/006 119/850 |

FOREIGN PATENT DOCUMENTS

| | | | | |
|---|---|---|---|---|
| GB | 2403124 | | 6/2005 | |
| GB | 2447839 | A * | 10/2008 | ........... A01K 13/008 |

* cited by examiner

OVINE PROTECTOR

CROSS-REFERENCE TO RELATED APPLICATIONS

The present application is U.S. national phase application under 35 U.S.C. § 371 of International Application No. PCT/AU2016/000056 filed Feb. 19, 2016, which claims priority to Australian Patent Application No. 2015900608 filed Feb. 20, 2015, the entire disclosures of which are incorporated by reference herein in their entireties for all purposes.

FIELD OF THE INVENTION

The present invention relates to an ovine protector for a newborn ovine. In particular the present invention relates to an ovine protector for a newborn ovine which substantially decreases mortality rate of newborn lambs from post-natal complications such as hypothermia due to effects of exposure.

The invention has been developed primarily for use in/with an ovine protector for substantially preventing hypothermia and premature mortality of newborn animals due to effects of exposure and will be described hereinafter with reference to this application. However, it will be appreciated that the invention is not limited to this particular field of use.

BACKGROUND OF THE INVENTION

Commercial success of a sheep farming operation depends upon maximising the number of lambs sold either for meat or as breeding stock while minimising costs of production. In turn, pounds of lamb weaned per ewe depend on saving newborn lambs. One of the critical points in the overall management of a flock therefore is lambing.

The largest percentage of lamb deaths occurs at or shortly after birth. Indeed it is suggested that 20% of lambs die before weaning, and of those about 80% of lamb mortality occurs during the first ten days following birth. Hence during lambing if at no other time during the year, investment of time and effective management practices is critical for a sheep producer to significantly reduce lamb mortality and thereby maximise economic return.

Main causes of lamb death following birth generally include hypothermia, starvation, and difficulty during the birthing process. Hypothermia is a condition in which a body's core temperature drops below that required for normal metabolism and body functions. This condition may result from a variety of factors including exposure, weakness, trauma, and starvation.

Lambs with hypothermia appear weak, gaunt, and hunched up. In severe cases, the lamb may be unable to hold its head up and may even be unconscious. The ears and mouth may feel cold, and the lamb may lack a suckling response. The normal body temperature for lambs is 102° to 103° F. Lambs with temperatures below 100° are considered hypothermic, and a rectal thermometer can be used to measure body temperature.

In newborn lambs, hypothermia may result from exposure. In these cases, it is necessary to a) get warm colostrum into the lamb immediately to bring its body temperature up, and b) to move the lamb into a warmer environment to elevate its body temperature.

Approaches generally used to elevate body temperature of a lamb include making sure the lamb is dried off if wet, and wrap it in a towel or blanket. While this is useful to a certain extent, it is often the case that if the lamb is still wet when the blanket is applied, the blanket allows expiration and condensation behind the blanket and thus can exacerbate the initial problem. Further, a blanket often fold over itself and leave air gaps, and covers a body to an extent where a parent ovine and even a farmer has limited if any direct access to the body of the lamb for identification purposes and other veterinary purposes and the like.

Other traditional methods of elevating temperature of a lamb include use of a hair dryer or even placing a lamb into a warming box. Makeshift warming boxes have included a cardboard box used to confine the lamb, with jugs of warm water used as a heat source. Other means of elevating temperature have included heat lamps although these are expensive and risk fire hence are generally not used routinely in a lambing barn.

Water baths have also been used to warm lambs, although the temperatures need to be carefully monitored so as not to use very hot water (>105° F.), which will warm the lamb too quickly and cause shock. In many instances, a farmer may even bring a lamb into a domestic dwelling and place in proximity to an open fireplace. While this is a relatively common practice to address hypothermia in newborn lambs, there are limits to the number of lambs not to mention the practical difficulties with the not so pleasant task of carrying lambs and exposure to covering of afterbirth.

There is thus a need to provide an improved means of addressing issues of hypothermia in newborn sheep so as to reduce lamb mortality and maximise profitability of sheep farming operation.

One object of the present invention therefore is to address one or more of the disadvantages of the prior art shower bases.

It is to be understood that, if any prior art information is referred to herein, such reference does not constitute an admission that the information forms part of the common general knowledge in the art, in Australia or any other country.

SUMMARY OF THE INVENTION

The present invention discloses an ovine protector for a newborn ovine including:
  a shaped body wrap providing a protection from the weather;
  a connection system for connecting the shaped body wrap to the newborn ovine, the connection system having a triangular arrangement between a front collar connection and two separate rear leg connections;
  wherein the protector provides a covering over the newborn ovine with an open rear and open underneath without crossover by the connection system to allow access by the ovine parent to relative locations on the newborn ovine for identification and interaction with the newborn ovine while maintaining effective body warmth.

The ovine protector of the present invention represents an improvement over the prior art practices. In particular, the ovine protector of the present invention provides an effective cover to allow protection from environmental elements such as wind and rain while enabling access anatomy for identification by a parent ovine, substantially maintaining the newborn ovine dry, while allowing free movement for walking.

The ovine protector of the present invention substantially reduces mortality rate of newborn lambs from immediate post-natal complications such as hypothermia due to effects of exposure in a much more practical and effective approach than the prior art.

In a related aspect, there is disclosed an ovine protector for a newborn ovine including:
- a shaped body wrap having a body cover portion, the shaped body providing a protection from the weather;
- a connection system connecting at extremities the shaped body wrap to the newborn ovine, the connection system having a triangular arrangement between a front collar connection and two separate rear leg connections;
- wherein the protector provides a covering over the newborn ovine with an open rear and open underneath by the connection system.

The connection system of the invention allow access by the parent ovine to relative locations on the newborn ovine for identification and interaction with the newborn ovine while maintaining effective body warmth without the need for a crossover connection which would otherwise hinder such access.

The front collar connection preferably comprises an elastic attachment interconnecting a pair of oppositely disposed collar portions to form an expandable collar. The elastic attachment can comprise a four-way stretch nylon lycra band.

In one embodiment the elastic attachment can distort the pair of oppositely disposed forward collar portions towards each other to form a neck portion which extends upwardly from the plane of the body cover portion to form front flaps. The front flaps protect a front or chest portion of the newborn ovine, and also allow free front leg movements of a newborn.

Preferably the rear leg connections are separately adjustable rear leg mounts fixed in a loop arrangement on opposite sides of the shaped body wrap. The triangular arrangement of the connection system allowing easy fitting of the ovine protector and removes the need for a cross over connection underneath or over the body which means that hindrance to access to umbilical cord for example is substantially avoided.

In a further embodiment of the present invention, a rear portion of the shaped body wrap can include a cut out or recess section for providing improved access to the rear of the newborn ovine for identification. In an operating condition, that is, in wearing, this recess forms a keyhole opening to allow ready access to a rear portion of the ovine newborn anatomy for a parent ovine in order to allow identification.

Preferably at least the body cover portion of the shaped body wrap includes a flexible sheet. The shaped body wrap can also include a protruding inverted u-shaped front collar portion formed at a front section of the flexible sheet body cover portion. This allows formation of downwardly extending flaps, wherein the flaps allow protection of the front of the newborn ovine while allowing unrestricted walking movement of the front legs of the newborn ovine.

Preferably the shaped body wrap comprises a laminate structure.

In a related aspect of the present invention there is disclosed an ovine protector for a newborn ovine, wherein the laminate structure shaped body wrap includes:
a. an outer shell comprising at least a layer of ePTFE, wherein the outer layer is substantially waterproof and resistant to ingress of wind, and
b. an inner liner layer adhered to the shell wherein the inner layer comprises of a material capable of wicking or moving moisture from the body surface of the newborn ovine towards the outer shell,
wherein the outer layer allows transfer of moisture from the newborn ovine to the environment so as to substantially maintain a dry body condition and substantially constant temperature for the newborn ovine.

In a further embodiment, the laminate structure shaped body wrap includes an outer shell having multiple layers including a Teflon coating bonded to fabric. The inner liner layer can be formed from a double sided material fabric which assists to expel moisture away from a newborn ovine body or skin, and circulate body heat more effectively. In an assembled form the outer shell and inner liner can be joined together by stitching.

The body cover can further include a pocket having an opening adjacent the rear cut out portion, wherein the pocket is adapted to receive a heating pad or the like, and includes an opening within the cut out section of the rear portion. The pocket can be sewn between the outer shell and inner liner.

The body cover can also further include an opening within the cut out section of the rear portion forming the opening to the pocket.

In yet a further related aspect of the present invention there is disclosed an active body cover for a newborn ovine to substantially reduce mortality rate of newborn lambs from immediate post-natal complications such as hypothermia due to effects of exposure, the body cover including:
- a shaped body wrap formed by a laminate material structure, the wrap comprising a body cover portion and u-shaped opening extending between a pair of oppositely disposed collar portions,
- a connection system comprising:
    - an elastic attachment interconnecting the oppositely disposed collar portions to form an expandable collar, wherein the elastic attachment distorts forward portions of the pair of collar portions towards each other and downwardly from the plane of the body cover portion to form front flaps which allow free front leg movements of a newborn;
    - a pair of adjustable rear leg mounts fixable in a loop arrangement on opposite sides of the body cover portion;
- wherein the active body cover includes an open rear and underneath for access to relative locations by a parent to allow identification of the newborn while maintaining effective body warmth such that newborn survival rates are improved.

A practical benefit of the cover of the invention is that the general requirement of the prior art to provide a cross-over connection, which otherwise may prevent access to the umbilical cord region by a parent, is omitted. This obviates hindrance to access to umbilical cord.

In a further related aspect there is disclosed an ovine protector comprising:
- a shaped body wrap providing a protection from the weather having:
    - a cut out section at a rear portion thereof for providing improved access to the rear of the newborn ovine for identification;
    - a body cover portion including a flexible sheet, and further including a pocket having an opening adjacent the rear cut out portion, wherein the pocket is adapted to receive a heating pad or the like, and includes an opening within the cut out section of the rear portion
- a connection system connecting at extremities the shaped body wrap to the newborn ovine, the connection system having a triangular arrangement between a front collar connection and two separate rear leg connections, wherein the front collar connection comprises an elastic attachment interconnecting a pair of oppositely disposed collar portions to form an expandable inverted u-shaped front collar, and wherein the elastic attachment distorts forward portions of the pair of oppositely disposed collar portions towards each other and downwardly from the plane of the body cover portion to form front flaps;

wherein the protector provides a covering over the newborn ovine with an open rear and open underneath by the connection system.

The elastic attachment distorts forward portions of the pair of oppositely disposed collar portions towards each other and downwardly from the plane of the body cover portion to form front flaps which cover chest portion while allowing free front leg movements of a newborn.

The shaped body wrap can comprises a laminate structure wherein the laminate structure preferably includes:

a. an outer shell comprising at least a layer of ePTFE, wherein the outer layer is substantially waterproof and resistant to ingress of wind, and b. an inner liner layer adhered to the shell wherein the inner layer comprises of a material capable of wicking or moving moisture from the body surface of the newborn ovine towards the outer shell.

In this embodiment, the outer layer allows transfer of moisture from the newborn ovine to the environment so as to substantially maintain a dry body condition and substantially constant temperature for the newborn ovine. The outer shell can also comprise multiple layers including a Teflon coating bonded to fabric, and the inner liner layer includes a double sided material fabric which assists to expel moisture away from a newborn ovine body or skin, and circulate body heat more effectively.

DESCRIPTION OF THE DRAWINGS

An embodiment of the present invention will now be described by way of example only with reference to the accompanying drawings in which.

DESCRIPTION OF THE PREFERRED EMBODIMENT WITH REFERENCE TO THE DRAWINGS

Figure 1:
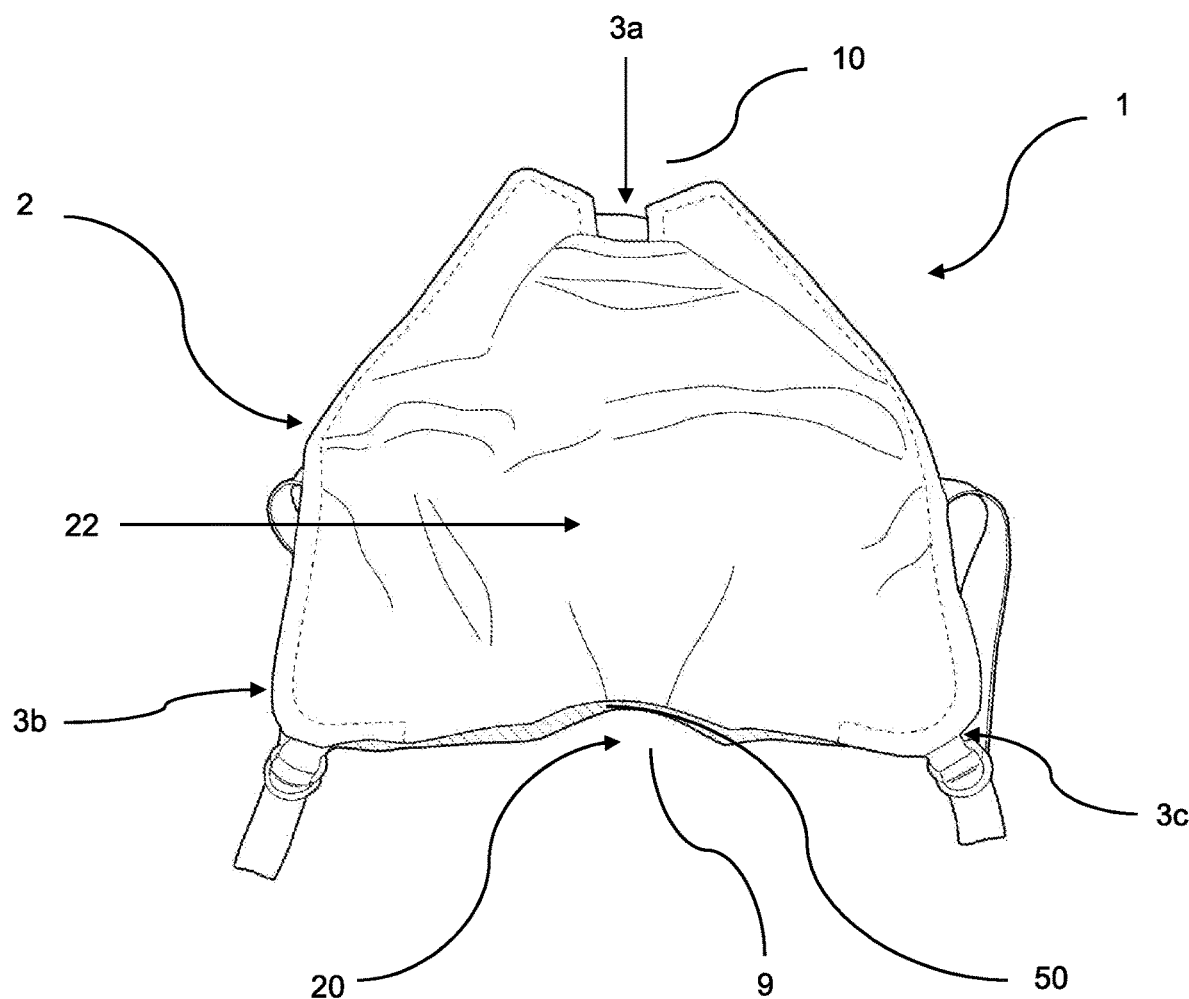
FIG. 1: is a photographic representation in part elevated rear view of an ovine protector in accordance with an embodiment of the invention.
Figure 2:
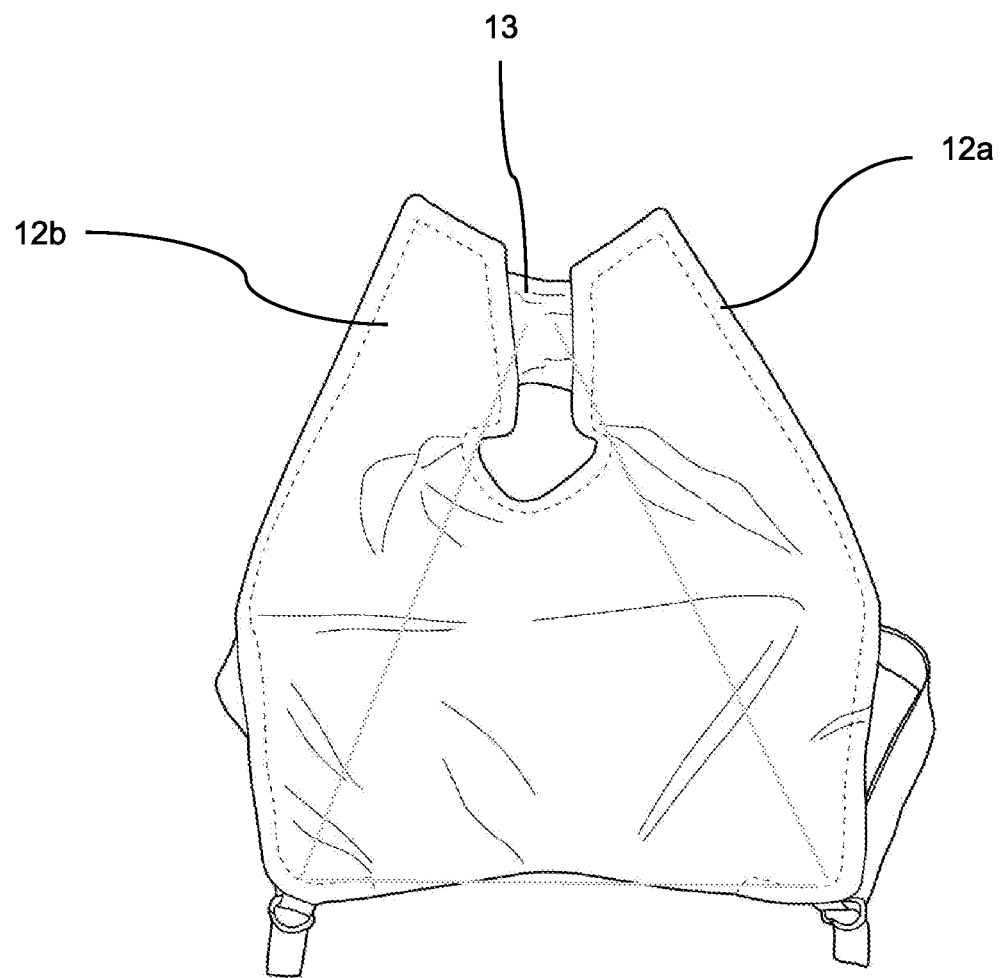
FIG. 2: is a photographic representation of the ovine protector in FIG. 1 in overhead plan view.
Figure 7:
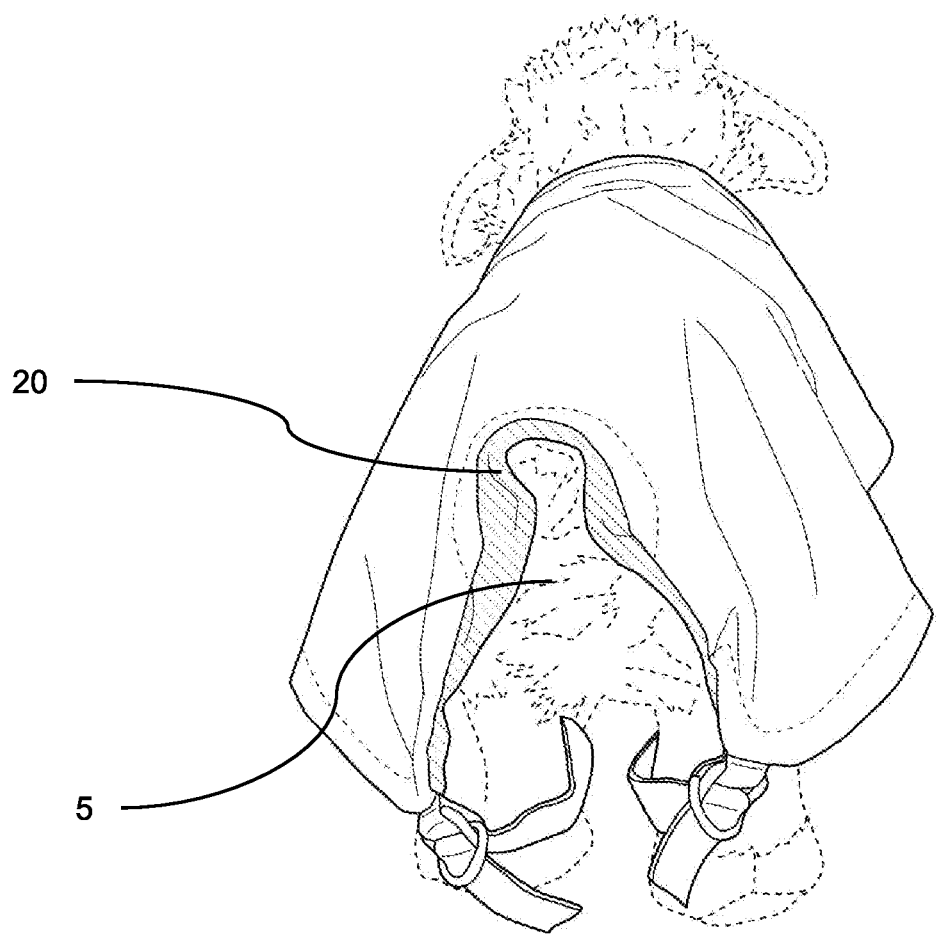
FIG. 7: shows a rear view of the ovine protector in FIGS. 1 to 6 in a wearing condition on a model toy lamb.
Figure 8:
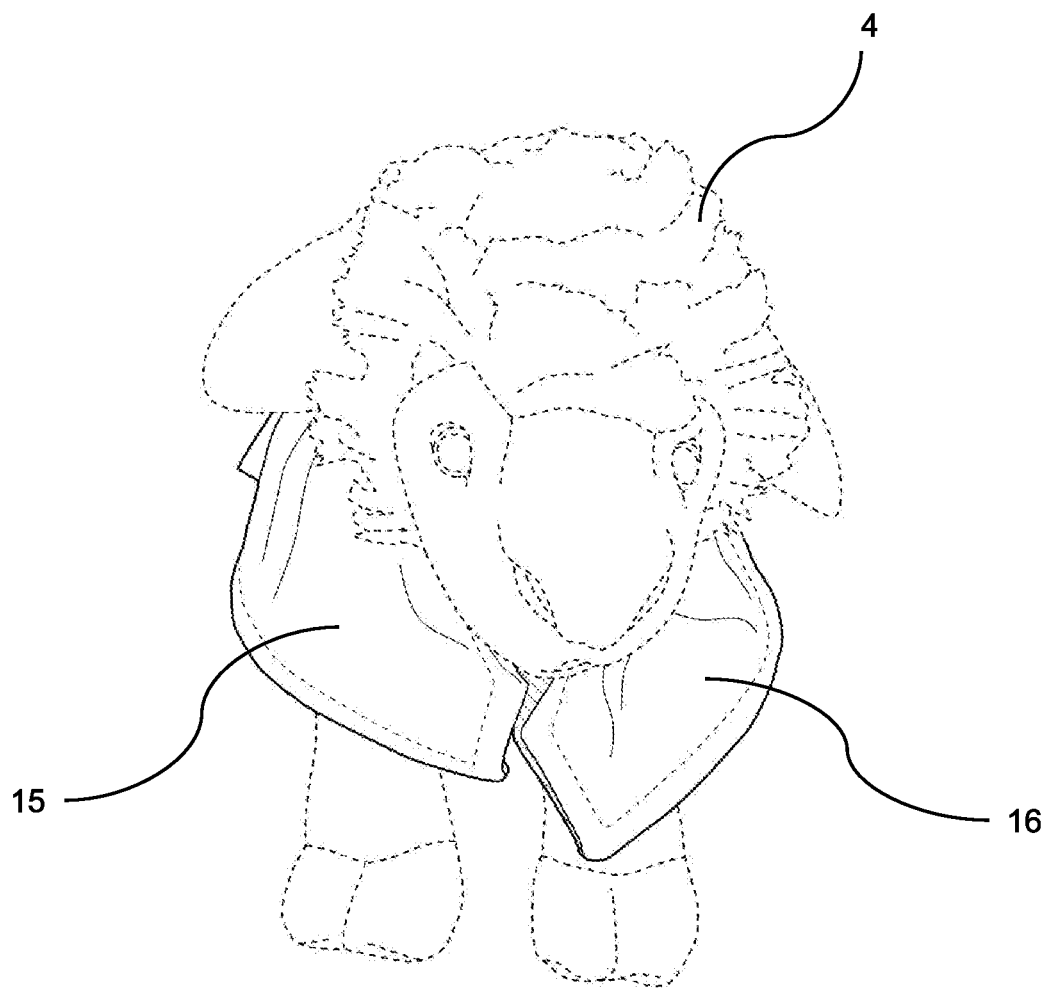
FIG. 8: shows a front view of the ovine protector in FIGS. 1 to 6 in a wearing condition on a model toy lamb.

Referring to FIGS. 1 to 6, there is shown an ovine protector 1 in accordance with one embodiment of the present invention. The ovine protector 1 includes a shaped body wrap 2 and a connection system 3a, 3b and 3c at extremities of the wrap for connecting the shaped body wrap 2 to the newborn ovine (see FIGS. 7 and 8) and so as to remove the requirement for a cross-over connection over or underneath the animal. As shown in FIG. 2, the connection system defines a triangular geometric arrangement between a front collar connection 3a and two separate rear leg connections 3b and 3c.

As shown in the figures, the shaped body wrap 2 of the ovine protector 1 includes a body cover portion 22 which provides a covering over the newborn ovine 4 with an open rear 5 and open underneath, without crossover by the connection system.

The shaped body wrap 2 has a general rectangular shape with a pair of oppositely disposed collar portions 12a and 12b at a front end portion thereof. In this embodiment the front collar connection comprises a stretchable lycra attachment 13 interconnecting the pair of oppositely disposed collar portions to form an expandable inverted u-shaped collar.

Figure 4:
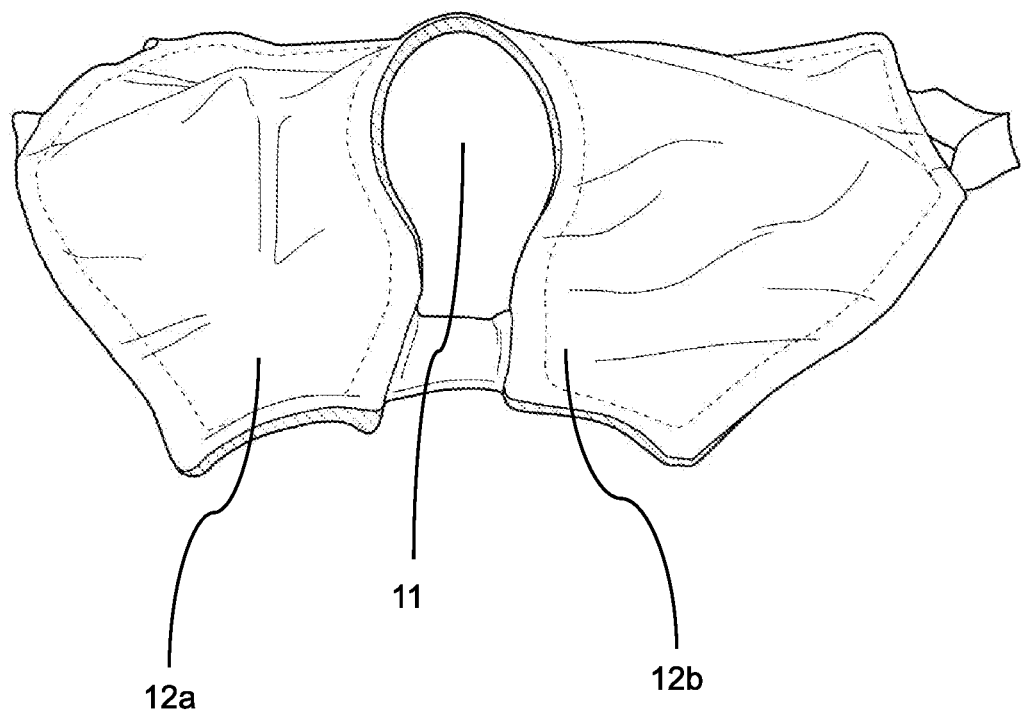
FIG. 4: is a photographic representation of the ovine protector in FIGS. 1 to 3 from a partial front elevation.
Figure 5:
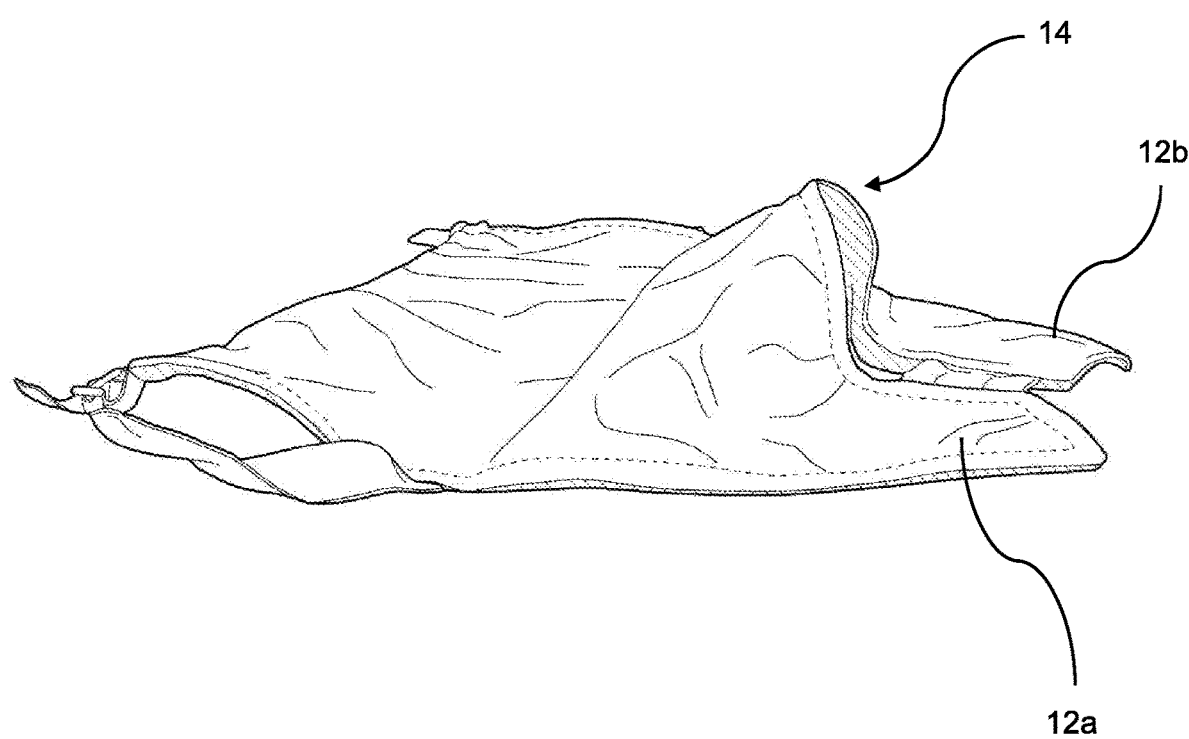
FIG. 5: is a photographic representation of the ovine protector in FIGS. 1 to 4 viewed from a partial side elevation.
Figure 6:
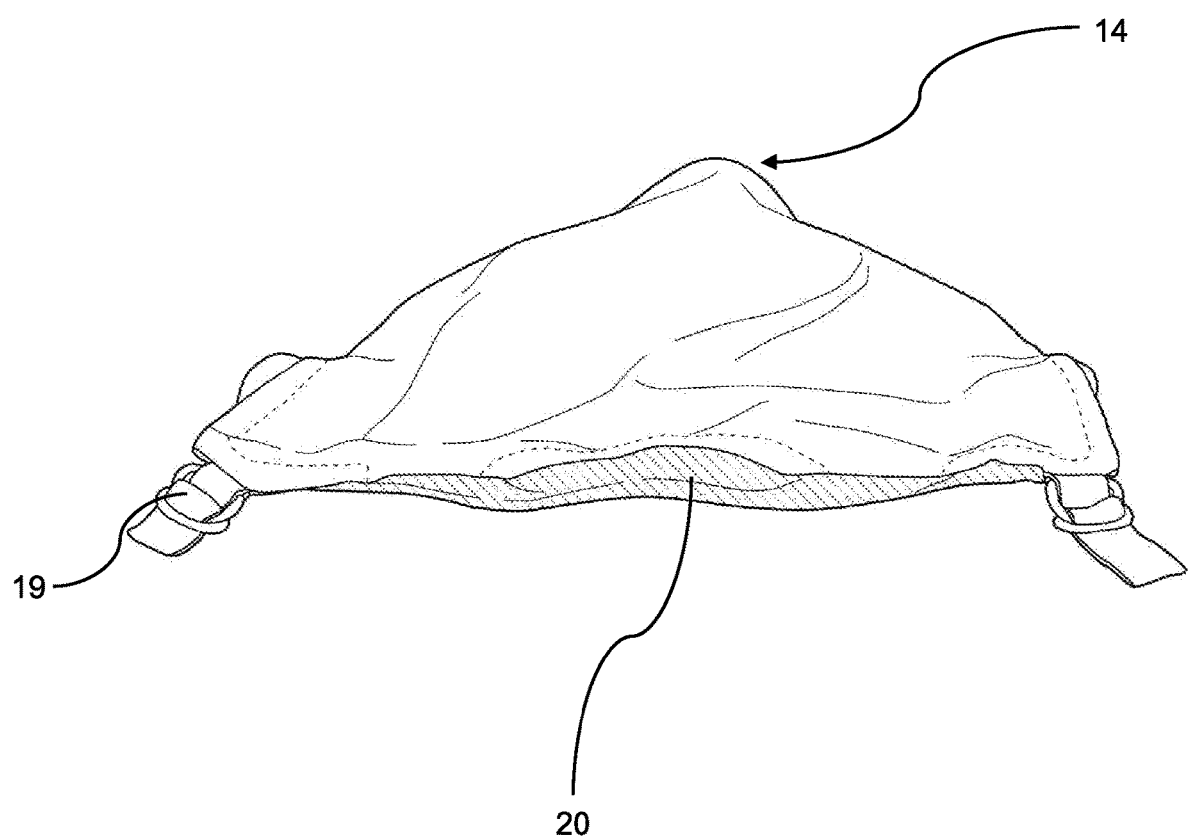
FIG. 6: is a photographic representation of the ovine protector in FIGS. 1 to 5 from a rear view.

As best seen in FIGS. 4, 5, and 6 the stretchable attachment 13 distorts forward portions of the pair of oppositely disposed collar portions 12 a and 12b towards each other and downwardly from the plane of the body cover portion to form front flaps which cover chest portion (see FIG. 8) while allowing free front leg movements of a newborn.

As best seen in FIG. 4, the front collar connection 3a is attached by stitching to inside portions of the pair of oppositely disposed front collar portions 12a and 12b so as to draw the opposite front collar portions towards each other. As seen in FIG. 5, the front collar attachment alters the general rectangular shape of the wrap by displacing the collar portions resulting in a forward structure 14 where the central opening 11 of the collar sits above the plane of the body cover portion 22.

As shown in FIGS. 4 and 5, the front collar portions 12a and 12b form front flaps 15 and 16 (see FIG. 8 in a wearing condition) which have a dual function to protect the front or chest region of the newborn ovine while allowing unhindered movement of front legs, it being critical to have a newborn ovine walking as soon as possible and any hindrance can prevent a lamb from moving between a prostrate position and an upright position for facilitating walking.

Figure 3:
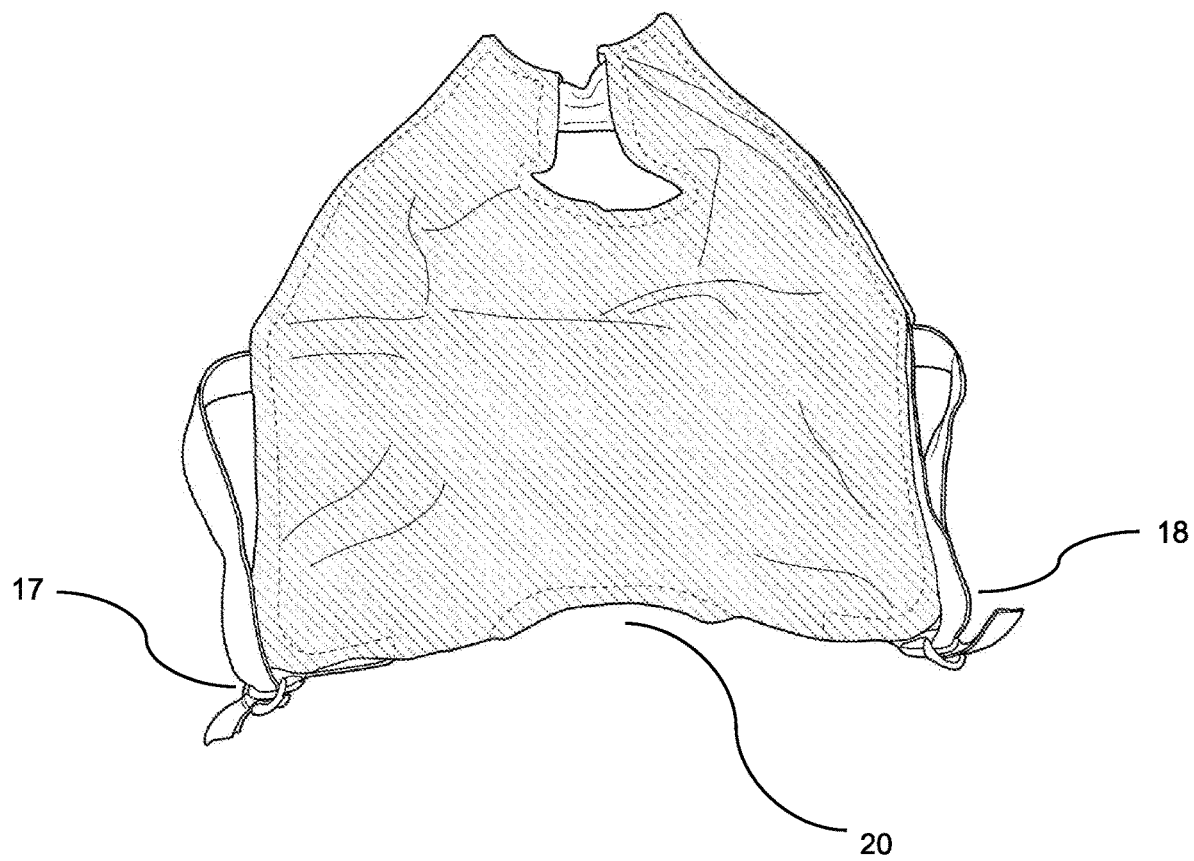
FIG. 3: is a photographic representation of underside of the ovine protector in FIGS. 1 and 2 in part elevated rear view.

The connection system in the present embodiment further includes rear leg connections 17 and 18 (best seen in FIG. 3). The leg connections include a buckle arrangement 19 stitched to the body wrap on opposite sides of the rear end portion thereof, and a ribbed elastic belting which is stitched to a portion of the body wrap forward of the buckle, and forms a loop configuration on opposite sides of the shaped body wrap when a part of the belt is passed through the buckle arrangement and fastened thereby.

As shown in FIGS. 1, 3, 6 and 7, a rear portion of the newborn ovine protector further includes a cut out section 20 centrally of the opposing buckle arrangements. When fitted to a newborn ovine (best seen in FIG. 7) a keyhole type structure 5 is formed allowing a parent ovine access to smell the end and therefore help identification of the lamb. It is important for a parent ovine to establish familial connection very quickly otherwise the newborn can become abandoned.

Prior art devices that hinder access break this connection, and this then requires reassimilation or grafting to a different parent ovine.

A clear benefit of the ovine protector is that it includes open rear and underneath, without cross-over connections so that the newborn can be allowed to walk, retain constant temperature and warmth, and allow access to rear quarters and umbilical cord for treatment.

Figure 9:
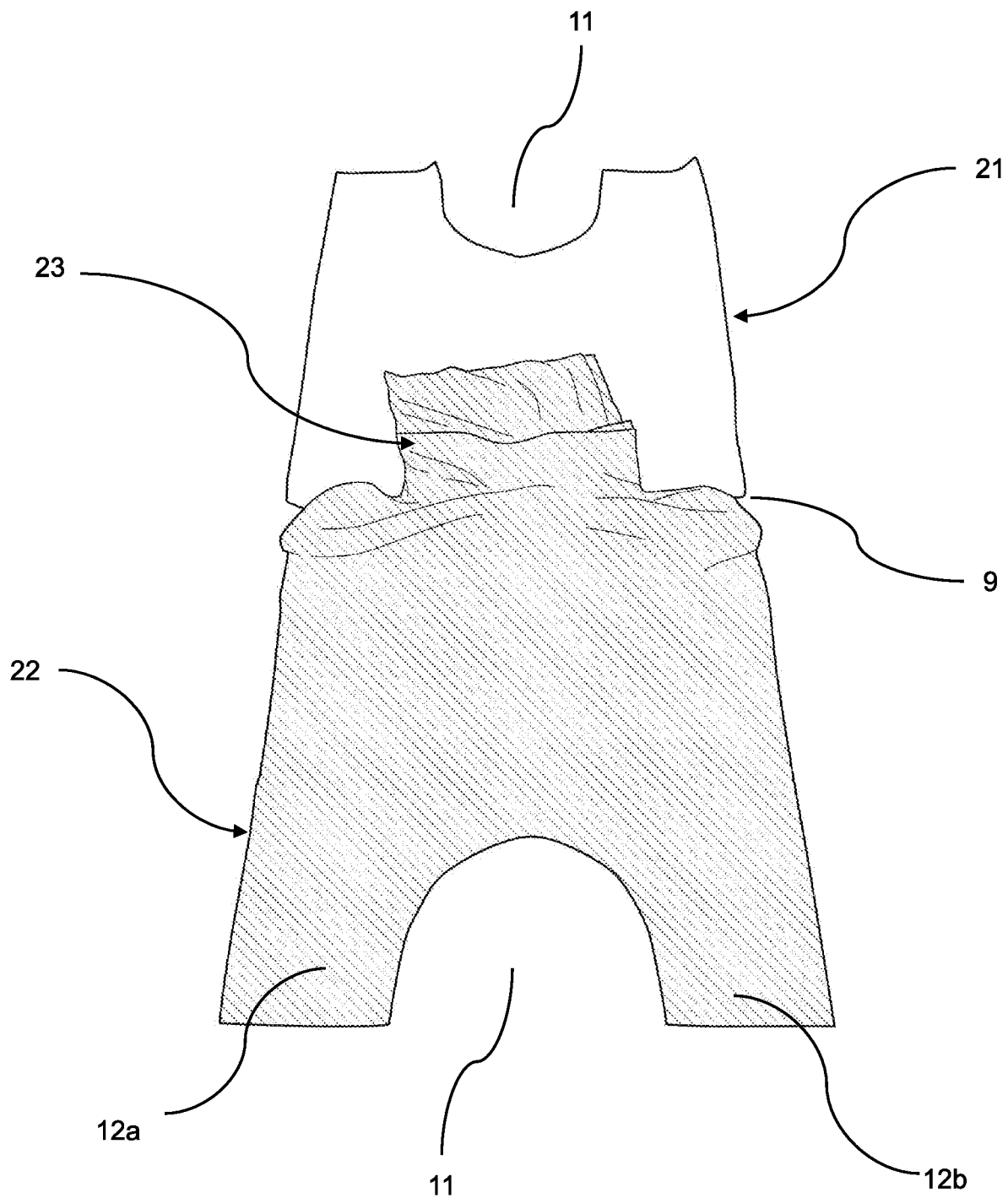
FIG. 9: shows a photographic representation of a partially assembled ovine protector.
Figure 10:
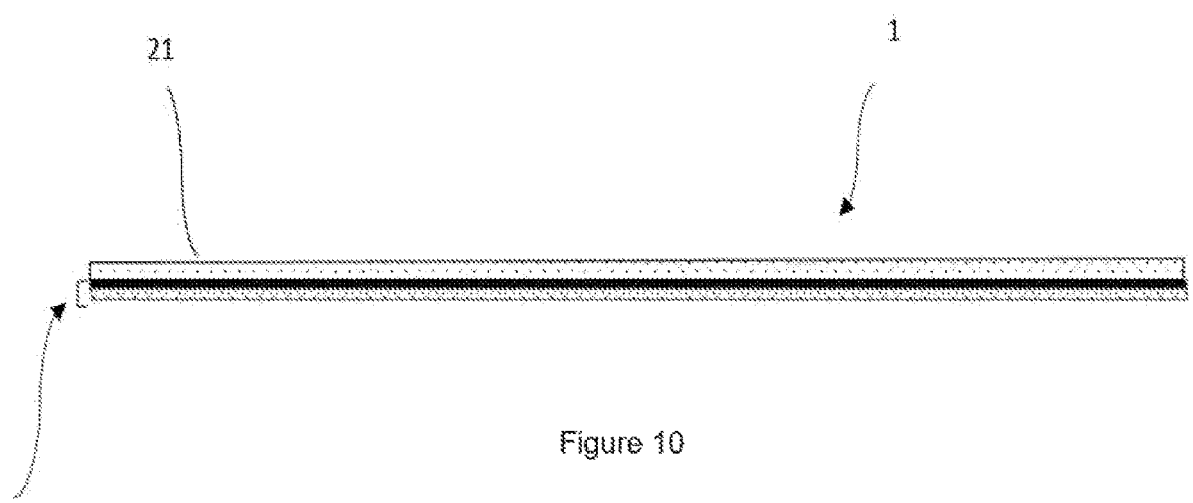
FIG. 10: is a schematic representation of a vertical cross-section of an ovine protector according to an embodiment of the present invention showing laminate layers.

In a further embodiment shown in FIGS. 9 and 10, the ovine protector 1 includes a laminate structure comprising an outer shell 21 and an inner liner 22. In FIG. 10 the cross-sectional schematic of the laminate structure shows inner liner 22 comprising a double sided fabric material which is adhered to an inner surface layer of the outer shell 21. The double-sided inner layer includes a material layer capable of wicking or moving moisture from the body surface of the newborn ovine towards the outer shell, which also allows more effective heat circulation about the body.

The outer shell 21 comprises multiple layers including a layer of ePTFE, wherein the outer layer is substantially waterproof and resistant to wind. In an operating condition the outer layer allows transfer of moisture from the newborn ovine to the environment so as to substantially maintain a dry body condition and substantially constant temperature for the newborn ovine. The outer shell in one embodiment further includes a layer of a Teflon coating bonded to fabric.

The ovine protector in partial assembled form (shown in FIG. 9), shows the outer shell 21 and inner liner 22 interconnected by stitching means along a rear end portion 9. The outer shell 22 is laid out above the inner liner and folded over with pocket 23 is sandwiched between the outer shell and inner liner with the pocket 23 having an opening located at within the rear cut out portion 20. The pocket is configured to generally follow the anatomical location of the newborn ovine kidneys. Peripheral edge portions of the outer shell and inner liner are stitched together to form the body wrap. In one embodiment (see FIG. 1), the pocket 23 of the ovine protector receives a heating pad 50 or the like therewithin. The heating pad or the like can be preheated and maintains warmth for an extended period.

The connection system is subsequently added to the body wrap to form a triangular connection system. And it is clear that when the collar connecting attachment 13 forms a bridge between the forward collar portions 12*a* and 12*b* to form a collar, the forward portions are brought closer together distorting the otherwise planar constructions shown in FIG. 9 to form upward extending structure 14 and forwardly protruding flaps 15 and 16.

In a further embodiment, the ovine protector includes a shaped body wrap formed by a laminate material structure, the wrap comprising a body cover portion and u-shaped opening extending between a pair of oppositely disposed collar portions. An elastic attachment interconnects the oppositely disposed collar portions to form an adjustable collar, and the elastic attachment distorts forward portions of the pair of collar portions towards each other and downwardly from the plane of the body cover portion to form front flaps which allow free front leg movements of a newborn. The protector includes a pair of adjustable rear leg mounts fixed in a loop arrangement on opposite sides of the body cover portion and wherein the active body cover includes an open rear and bottom without cross over for access to relative locations by a parent to allow identification of the newborn while maintaining effective body warmth such that newborn survival rates are improved.

The present invention provides the following benefits:
provides a protective body cover for a newborn ovine which substantially reduces mortality rate of newborn lambs from immediate post-natal complications such as hypothermia due to effects of exposure,
Addresses problems with traditional methods by improved structure to allow optimal coverage of body area while enabling easy walking without hindrance, critical access to the rear and underneath
Provide a stable or constant temperature with heat circulation effect:
Ovine production rates are significantly higher hence improved economies of scale
ovine protector includes open rear and underneath, without cross-over connections so that the newborn can be allowed to walk, retain constant temperature and warmth, and allow access to rear quarters and umbilical cord for treatment
helps maintain dry body while effective waterproofing from weather Interpretation Embodiments:

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the field of newborn animal husbandry.

The invention claimed is:

1. An ovine protector for a newborn ovine comprising:
a shaped body wrap having a body cover portion, the shaped body wrap providing a protection from ambient weather conditions;
a pair of oppositely disposed collar portions extending forwardly of the body cover portion;
a connection system connecting at extremities the shaped body wrap to the newborn ovine, the connection system having a triangular arrangement between a front collar connection and two separate rear leg connections;
wherein the protector provides a covering over the newborn ovine with an open rear and open underneath by the connection system;
wherein the front collar connection comprises an elastic attachment interconnecting the pair of oppositely disposed collar portions to form an expandable collar; and
wherein the elastic attachment distorts the pair of oppositely disposed collar portions towards each other and downwardly from the plane of the body cover portion, and wherein the pair of oppositely disposed collar portions extend downwardly covering the chest region in a side by side abutting relation by the elastic attachment to form front flaps which cover a chest portion of the newborn ovine while allowing free front leg movements of a newborn.

2. The ovine protector for a newborn ovine according to claim 1, wherein the rear leg connections are separate adjustable rear leg mounts fixable in a loop arrangement on opposite sides of the shaped body wrap.

3. The ovine protector for a newborn ovine according to claim 1, wherein a rear portion of the shaped body wrap comprises a cut-out section for providing improved access to the rear of the newborn ovine for identification by a parent.

4. The ovine protector for a newborn ovine according to claim 3, wherein the body cover portion further comprises a pocket having an opening adjacent the rear cut-out portion, wherein the pocket is adapted to receive a heating pad, and includes an opening within the cut-out section of the rear portion.

5. The ovine protector for a newborn ovine according to claim 1, wherein at least the body cover portion of the shaped body wrap comprises a flexible sheet.

6. The ovine protector for a newborn ovine according to claim 1, wherein the pair of oppositely disposed collar portions are distorted by the elastic attachment upwardly from the plane of the body cover portion forming an inverted u-shaped front collar portion.

7. The ovine protector for a newborn ovine according to claim 1, wherein the shaped body wrap comprises a laminate structure.

8. The ovine protector for a newborn ovine according to claim 7, wherein the laminate structure shaped body wrap comprises:
a. an outer shell comprising at least a layer of ePTFE, wherein the outer layer is substantially waterproof and resistant to ingress of wind, and
b. an inner liner layer adhered to the shell wherein the inner layer comprises of a material capable of wicking or moving moisture from the body surface of the newborn ovine towards the outer shell,
wherein the outer layer allows transfer of moisture from the newborn ovine to the environment so as to substantially maintain a dry body condition and substantially constant temperature for the newborn ovine.

9. The ovine protector for a newborn ovine according to claim 8, wherein the outer shell comprises multiple layers including a PTFE coating bonded to fabric, and the inner liner layer includes a double-sided material fabric which assists to expel moisture away from a newborn ovine body or skin, and circulate body heat more effectively.

10. A body cover for a newborn ovine to substantially reduce mortality rate of newborn lambs from immediate post-natal complications such as hypothermia due to effects of exposure, the body cover comprising:
a shaped body wrap formed by a laminate material structure, the wrap comprising a body cover portion and a front collar connection comprising a pair of oppositely disposed collar portions extending forwardly of the body cover portion, and an elastic attachment interconnecting the pair of oppositely disposed collar portions to form an expandable collar having a u-shaped opening extending between the oppositely disposed collar portions;

a connection system connecting at extremities the shaped body wrap to the newborn ovine, the connection system having a triangular arrangement between the front collar connection and two separate rear leg connections;

wherein the shaped body wrap includes:
 a cut out section at a rear portion thereof for providing improved access to the rear of the newborn ovine for identification by a parent; and
 a pocket having an opening adjacent the rear cut out portion, wherein the pocket is adapted to receive a heating pad, and includes an opening within the cut out section of the rear portion;

wherein the elastic attachment of the front collar connection distorts the pair of collar portions towards each other and downwardly from the plane of the body cover portion and wherein the pair of oppositely disposed collar portions extend downwardly covering the chest region in an abutting relation by the elastic attachment to form front flaps which covers a chest region of the ovine in use and allows free front leg movements of the newborn ovine;

the rear leg connections being adjustable fixed in a loop arrangement on opposite sides of the body cover portion; and wherein the body cover comprises an open rear and underneath by the connection system for access to relative locations by a parent to allow identification of the newborn while maintaining effective body warmth such that newborn survival rates are improved.

11. The body cover for a newborn ovine according to claim 10, wherein the laminate material structure comprises:
 a. an outer shell comprising at least a layer of ePTFE, wherein the outer layer is substantially waterproof and resistant to ingress of wind, and
 b. an inner liner layer adhered to the shell wherein the inner layer comprises of a material capable of wicking or moving moisture from the body surface of the newborn ovine towards the outer shell.

12. The body cover for a newborn ovine according to claim 11, wherein the outer shell comprises multiple layers including a PTFE coating bonded to fabric, and the inner liner layer comprises a double-sided material fabric which assists to expel moisture away from a newborn ovine body or skin, and circulate body heat more effectively.

13. The body cover for a newborn ovine according to claim 10, wherein the rear leg connections are separate adjustable rear leg mounts fixable in a loop arrangement on opposite sides of the shaped body wrap.

14. The body cover for a newborn ovine according to claim 10, wherein at least the body cover portion of the shaped body wrap comprises a flexible sheet.

15. The body cover for a newborn ovine according to claim 10, wherein the pair of oppositely disposed collar portions are distorted by the elastic attachment upwardly from the plane of the body cover portion forming an inverted u-shaped front collar portion.

16. An animal protector for a newborn comprising:
a shaped body wrap having:
 a body cover portion; and
 a front collar connection comprising a pair of spaced apart oppositely disposed collar portions extending forwardly from the body cover portion and an elastic attachment interconnecting the pair of oppositely disposed collar portions to form an expandable collar, wherein the elastic attachment distorts forward portions of the pair of oppositely disposed collar portions towards each other and downwardly from the plane of the body cover portion, and wherein the pair of oppositely disposed collar portions extend downwardly covering the chest region in an abutting relation by the elastic attachment to form front flaps which cover a chest portion of the newborn ovine while allowing free front leg movements;
 wherein a rear portion of the body cover portion comprises:
  a cut-out section for providing improved access to the rear of the newborn ovine for identification by a parent; and
  a pocket having an opening adjacent the rear cut-out portion, wherein the pocket is located over kidney region of the animal in use, and
 is adapted to receive a heating pad over the kidney region; and
a connection system connecting at extremities the shaped body wrap to the newborn ovine, the connection system having a triangular arrangement between the front collar connection and two separate rear leg connections;

wherein in use the body cover portion extends over the body of the newborn animal, and the forward portions of the pair of oppositely disposed collar portions forming the flaps project downwardly as a result of the distortion caused by the front collar connection to cover chest portion of the animal while allowing free front leg movements of the newborn; and wherein the protector provides a covering over the newborn ovine with an open rear and open underneath by the connection system.

17. The animal protector for a newborn according to claim 16, wherein the rear leg connections are separate adjustable rear leg mounts fixable in a loop arrangement on opposite sides of the shaped body wrap.

18. The animal protector for a newborn according to claim 16, wherein at least the body cover portion of the shaped body wrap comprises a flexible sheet.

19. The animal protector for a newborn according to claim 16, wherein the pair of oppositely disposed collar portions are distorted by the elastic attachment upwardly from the plane of the body cover portion forming an inverted u-shaped front collar portion.

20. The animal protector for a newborn according to claim 16, wherein the shaped body wrap comprises a laminate structure.

* * * * *